US006244268B1

(12) United States Patent
Annett et al.

(10) Patent No.: US 6,244,268 B1
(45) Date of Patent: Jun. 12, 2001

(54) SURGICAL DRAPE CONFIGURATION AND PACKAGE

(75) Inventors: Leland W. Annett; David B. Padget, both of Stillwater, MN (US)

(73) Assignee: Medical Concepts Development, Inc., Woodbury, MN (US)

( * ) Notice: Subject to any disclaimer, the term of this patent is extended or adjusted under 35 U.S.C. 154(b) by 0 days.

(21) Appl. No.: 09/277,895

(22) Filed: Mar. 29, 1999

(51) Int. Cl.[7] ................................................. A61B 19/00

(52) U.S. Cl. ............................................ 128/849; 128/856

(58) Field of Search ................................. 128/849–856

(56) References Cited

U.S. PATENT DOCUMENTS

| 5,730,994 | * | 3/1998 | Askill | 424/402 |
| 5,957,877 | * | 9/1999 | Askill | 602/54 |

FOREIGN PATENT DOCUMENTS

WO 98/16167 * 4/1998 (WO).

* cited by examiner

Primary Examiner—Michael A. Brown
(74) Attorney, Agent, or Firm—Nawrocki, Rooney & Sivertson, P.A.

(57) ABSTRACT

A configuration of surgical drapes for convenient dispensing and handling from a container. The configuration includes a continuous rolled length of surgical drapes having opposing major and minor longitudinal edges. Each drape of the continuous roll is separable from adjacent drapes by longitudinally spaced apart lines of weakness throughout the continuous length of surgical drapes. The continuous rolled length of surgical drapes includes an adhesive strip adjacent the major longitudinal edge of the continuous rolled length of surgical drape. The adhesive strip in turn carries a removable release liner thereover which preferably partially overhangs the adhesive strip. The continuous rolled length of surgical drapes further has an accordion pleat fold to thereby reduce the stored and dispensed width of each drape of said continuous length of surgical drapes.

13 Claims, 3 Drawing Sheets

SURGICAL DRAPE CONFIGURATION AND PACKAGE

TECHNICAL FIELD

The present invention relates broadly to surgical drapes. More particularly, however, the invention relates to a surgical drape configuration and package permitting compact surgical drape storage for convenient dispensing and handling, and methods of dispensing and making same.

BACKGROUND OF INVENTION

Surgical drapes are known to have a variety of uses during all aspects of surgical operations. It is not uncommon to consume a great number of drapes even for the most elementary of procedures. Efficient and reliable storage, dispensing and deployment of bulk quantities of surgical drapes is most desirous. Heretofore, surgical drapes have been provided as sterile, individually folded and packaged products or as individually folded, non-sterile bulk packaged products.

As surgical drapes have both sterile and non-sterile uses, use of the more convenient but package intensive individually folded and wrapped sterile drapes in non-sterile applications has proven cost prohibitive. The unit costs of individually folded and wrapped drapes are high because of additional and sometimes elaborate packaging that is provided and oftentimes required. This, in combination with the fact that operating room storage space is typically at a premium and room for surgical drapes a low priority, makes bulk packaging of surgical drapes an attractive alternative.

Non-sterile bulk packed surgical drapes have had limited success as their packaging is generally not permitted in the operating room because they do not pass a minimum cleanliness threshold. When the bulk drapes are removed from their packaging or cartons, which can be a chore in and of itself, they are difficult to maintain in an orderly manner, usually becoming an unusable jumble of material. Furthermore, bulk storage exposes the entire supply to grasping hands in the operating room which may inadvertently cross contaminate remaining drapes of the bulk supply and thereby render them unusable.

It is thus desirous and advantageous to provide a convenient way to store a greater density of surgical drapes and deliver individual drapes from a supply of surgical drapes in a neat, quick, efficient and reliable manner.

SUMMARY OF THE INVENTION

The present invention is configuration of surgical drapes for convenient dispensing and handling from a container. The configuration comprises a continuous rolled length of surgical drapes having opposing major and minor longitudinal edges. Each drape of the continuous roll is separable from adjacent drapes by longitudinally spaced apart lines of weakness throughout the continuous length of surgical drapes. The continuous rolled length of surgical drapes includes an adhesive strip adjacent the major longitudinal edge of the continuous rolled length of surgical drape. The adhesive strip in turn is equipped with a removable release liner thereover which preferably partially overhangs the adhesive strip. The continuous rolled length of surgical drapes has a fold to thereby reduce the stored and dispensed width of each drape of said continuous length of surgical drapes.

The fold generally takes the form of an accordion pleat, more particularly the fold forms overlying adjacent longitudinal drape panels. These panels are delimited by spaced apart longitudinal creases and have a collapsed zig-zag cross section. The minor longitudinal edge is positioned to be retained under the overhang of the removable release liner for especially easy handling and deployment (i.e., unfolding) of a dispensed drape.

In a preferred embodiment, the configuration of surgical drapes is provided in combination with a container such that configuration of surgical drapes is removably housed therein for easy dispensing of at least one drape from the configuration of surgical drapes. The container generally includes a base joined to a cover at a common hinge to permit closure of the cover about the configuration of surgical drapes placed on the base. A drape dispensing mouth is formed opposite the common hinge and is configured to hold the outer most drape of the configuration of drapes in a position for easy grabbing and removal from the continuous rolled length of surgical drapes.

More specifically, a package of surgical drapes is provided and includes a container having a base connected to a cover by a common hinge and a continuous rolled length of surgical drapes removably housed therein. The continuous rolled length of surgical drapes has opposing major and minor longitudinal edges. Each drape of said continuous roll being separable from adjacent drapes by longitudinally spaced apart lines of weakness throughout said continuous length of surgical drapes for easy dispensing of at least one drape from said continuous rolled length of surgical drapes. The continuous rolled length of surgical drapes further has a fold to thereby reduce the stored and dispensed width of each drape of the continuous length of surgical drapes.

A method of storing and dispensing surgical drapes from a container is provided including the steps of: supplying a continuous length of surgical drapes having a uniform width where the drapes are separable by longitudinally spaced apart lines of weakness; folding the continuous length of surgical drapes in a manner to reduce the uniform width; rolling the reduced width continuous length of surgical drapes; providing a container having a base and a cover where the cover is joined to the base at a common hinge for closure of the cover; and housing the rolled reduced width continuous length of surgical drapes within the container for dispensing at least one drape from the configuration of surgical drapes.

Finally, in a method of manufacturing a continuous rolled length of surgical drapes for convenient dispensing and handling, the steps of accordion folding the longitudinal edges of a supply of drape material towards the centerline of the supply; and cutting the supply along said centerline to thereby form two lengths of fan folded surgical drape material.

DETAILED DESCRIPTION OF THE INVENTION

Figure 1:
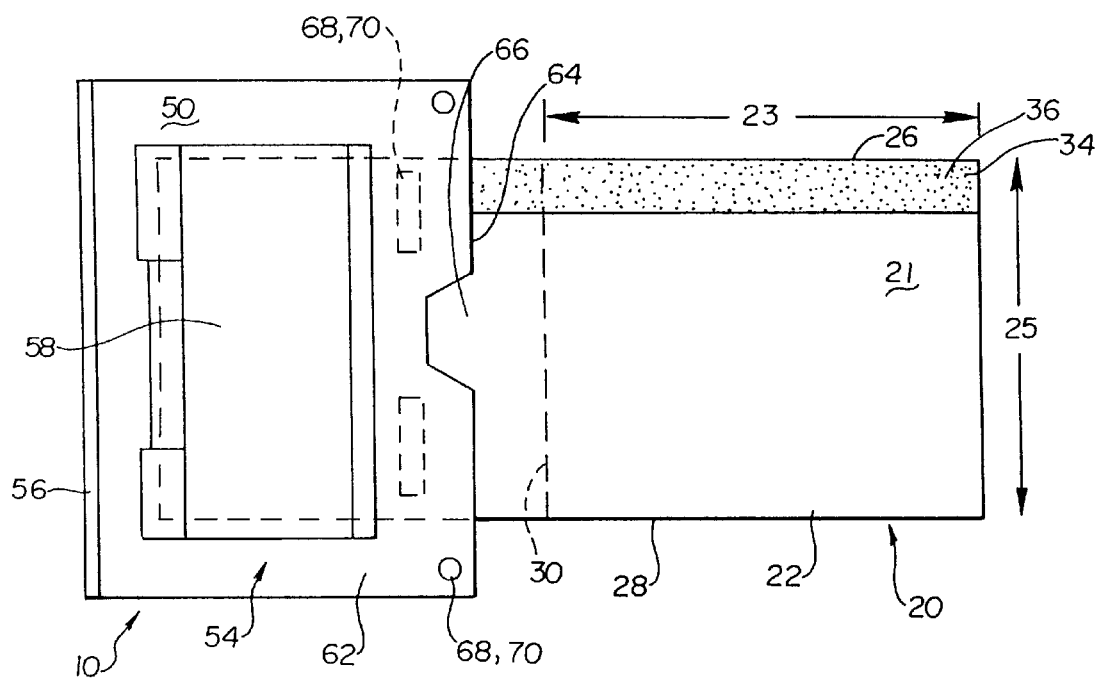
FIG. 1 is a plan view of a package of specially configured surgical drapes.
Figure 2:
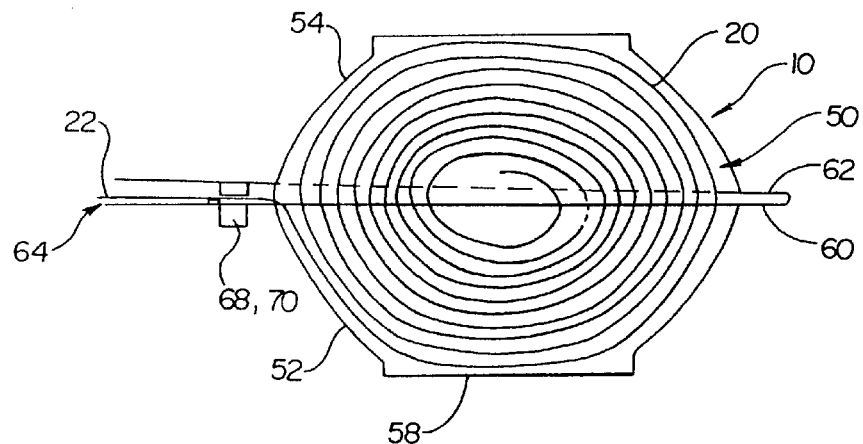
FIG. 2 is a sectional view taken along section line 2—2 of FIG. 1.

Referring now to the drawings wherein like reference numerals denote like elements throughout the several views, FIGS. 1 & 2 illustrate a package of surgical drapes in plan and sectional views respectively. The package 10 generally includes a special configuration of surgical drapes 20 housed within a container 50, with at least a portion of the end or outer most drape 22 of the supply 20 being accessible for dispensing therefrom. The supply of drapes 20 are provided in a continuous rolled length format having a special configuration permitting convenient dispensing and handling, whether or not a container is used. The continuous rolled length of drapes 20 generally has a width 25 and opposing major 26 and minor 28 longitudinal edges. Each drape 21 of the continuous rolled length of surgical drapes 20 is separable from adjacent drapes by lines of weakness 30. The lines of weakness 30 are longitudinally spaced apart throughout the continuous length of surgical drapes 20 to permit the easy tear removal of single or multiple drapes from the supply of drapes, and or from each other.

Figure 3:
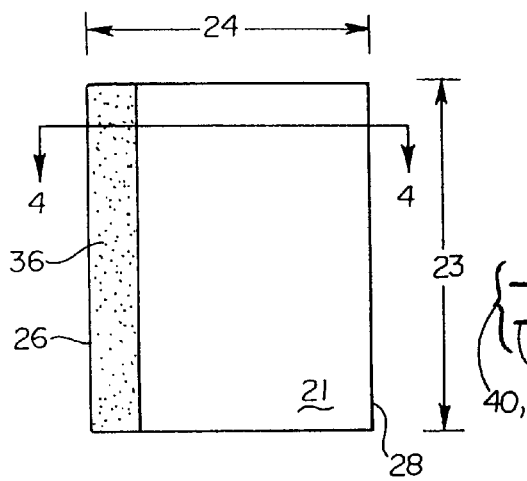
FIG. 3 is a plan view of a just dispensed surgical drape ready for deployment.
Figure 4:
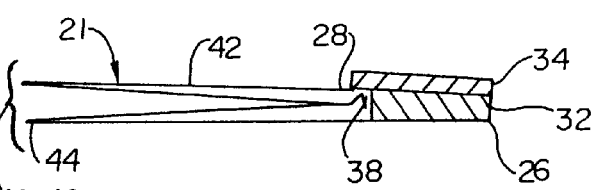
FIG. 4 is a sectional view taken along section line 4—4 of FIG. 3.
Figure 5:
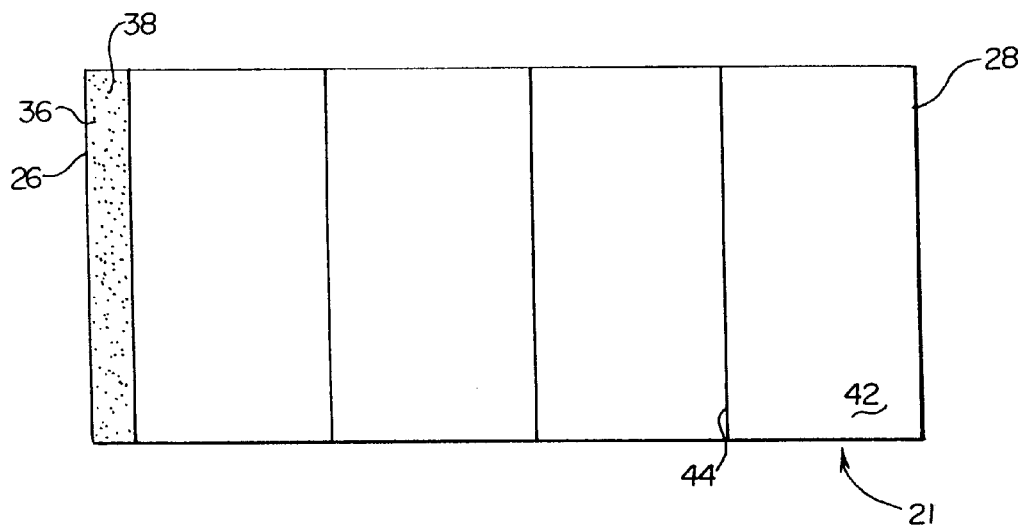
FIG. 5 is a plan view of a deployed surgical drape dispensed from the specially configured supply.

FIGS. 3–5 illustrate a single drape of the configuration of surgical drapes. A layer of adhesive 32 (i.e., an adhesive strip) is preferably included and positioned adjacent to the major 26 longitudinal edge of the continuous rolled length of surgical drapes 20. The adhesive strip 32 permits sure positioning of a single drape to, or in a work area, as well as affixation of single drapes to each other to create greater drape coverage in a work area. The adhesive strip 32 is equipped with a removable release liner 34 thereover, and may be adapted to carry printed matter 36 denoting the drapes as being "sterile" or "non-sterile" or other indicia believed to have significance to the users of such articles. Preferably the release liner 34 has a portion 38 overhanging the adhesive strip 32 on its inner longitudinal limit.

As is best illustrated in FIG. 4, the continuous rolled length of surgical drapes 20 has a fold 40 throughout its length to thereby reduce the stored and dispensed width of each drape 21 of the specially configured supply 20. The fold 40 generally resembles an accordion pleat. More specifically, the fold 40 forms overlying adjacent longitudinal drape panels 42, each of the panels 42 being separated by spaced apart longitudinal creases 44. The fold 40 produces a collapsed or flattened zig-zag cross section 46 for the continuous rolled length of surgical drapes 20 wherein the overlying or collapsed panels 42 do not overlap or otherwise interfere with the adhesive strip 32. However, the overhanging portion 38 of the release liner 34 creates a crotch (i.e., the space between the overhanging portion 38 of the release liner 34 and the laterally extending drape panel 42 thereunder) for receipt of the outer edge of the uppermost panel 28 (i.e., the minor longitudinal edge 28 of the continuous length of surgical drapes 20). This arrangement permits "tucking" the minor longitudinal edge 28 of the folded length of surgical drapes 20 under the overhanging release liner 34 to thereby form a neatly configured, easily dispensed drape 21 that does not immediately unfold and become messy to handle. Furthermore, the overhanging release liner 34 permits an easy finger hold to facilitate removal of it from the adhesive 32 for affixation of the drape as is typically required.

FIG. 5 illustrates a dispensed and deployed (i.e., unfolded for use) single drape 21 of the preferred embodiment having a overall length 23 and width 25, four drape panels 42 and three creases 44. Assigning increasing numbers to the panels 42 from the minor longitudinal edge 28 to the major longitudinal edge 26 of the continuous length of surgical drape 20, the first drape panel is turned about the first longitudinal crease such that the top surface of the first drape panel substantially covers the top surface of the second drape panel. The second drape panel is turned about the second longitudinal crease such that the bottom surface of the second drape panel substantially covers the bottom surface of the third drape panel. The third drape panel is thereafter turned about the third longitudinal crease such that the top surface of the third drape panel covers a majority of the top surface of the fourth panel without overlapping the adhesive layer. Using this nomenclature, the fourth panel is the uppermost overlying drape panel, the panel that is tucked under the overhanging release liner 34 as shown in FIG. 4.

Figure 6:
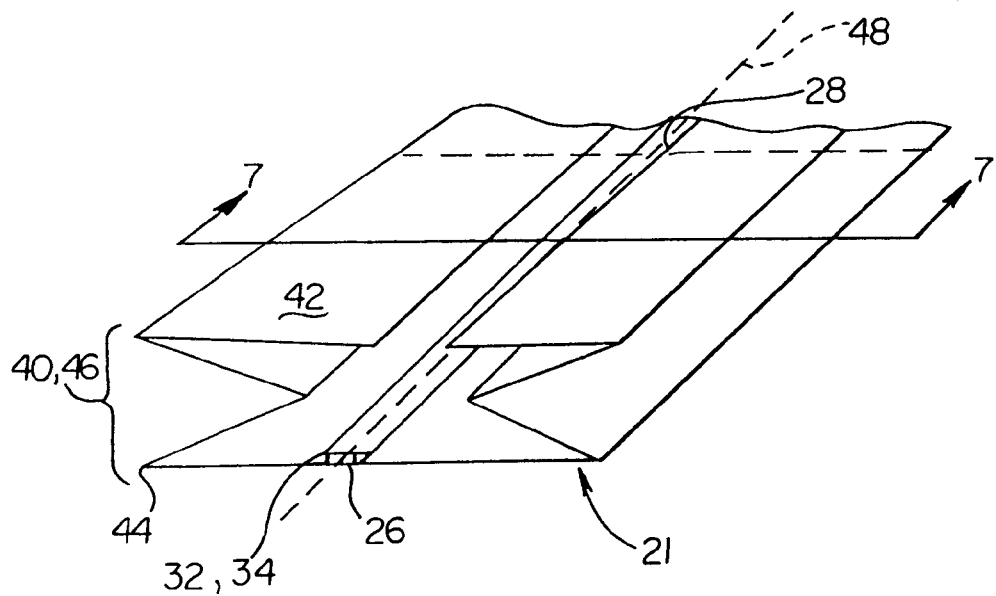
FIG. 6 is a partial perspective view illustrating the manner of producing the folded supply of surgical drapes.
Figure 7:
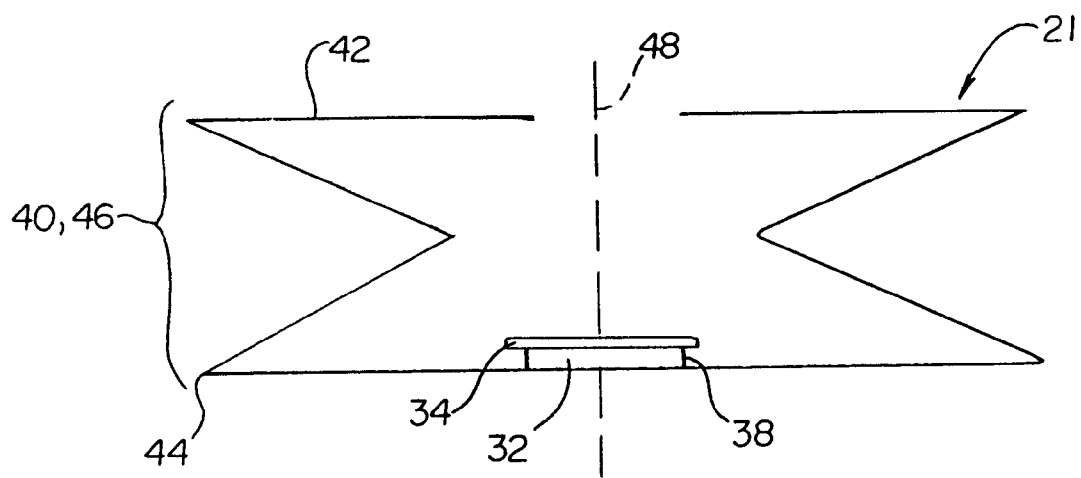
FIG. 7 is a sectional view taken along section line 7—7 of FIG. 6.

FIGS. 5 & 6 illustrate the general manner in which the specially configured continuous rolled length of surgical drapes is formed. A continuous length of surgical drape material having an adhesive strip 32 straddling the longitudinal centerline 48 thereof is symmetrically accordion folded about the longitudinal center line 48 in a manner to produce the overlying adjacent longitudinal drape panels 42 hereinabove described. The release liner 34 is next applied over the adhesive strip 32 and the continuous length of drape material may then be scored or perforated (i.e., line of weakness 30 formed) at laterally spaced apart intervals to thereby establish the width 25 for each drape 21 of the continuous rolled supply of drapes 20. Finally, the supply of drape material so manipulated is cut or otherwise separated along its longitudinal centerline 48 to thereby form two mirror imaged intermediate products suited for further processing.

Returning again to FIGS. 1, 2 & 2A, the container 50 for removably housing the configuration of surgical drapes 20 includes a base 52 joined to a cover 54 by a common hinge 56. For the most part, the cover 54 and base 52 are symmetrical. It is important that at either the base 52 or the cover 54 have a substantially flat surface portion 58 so as to be set down, confident that the package will not roll, be readily displaced or otherwise travel. Both the container base 52 and cover 54 have flanged portions 60 & 62 extending thereabout. The interface of the flanged cover 62 and base 60 portions opposite the hinge 56 generally forms a drape dispensing mouth 64. The mouth 64 is configured to hold the outer most drape 22 of the configuration of drapes 20 in a position for easy grabbing and removal from the continuous rolled length of surgical drapes 20. The flanged portions 60 & 62 forming the container mouth 64 further include alignable notches 66 which provide a finger hold for a drape being held for dispensing should such a drape not extend or protrude beyond and from the mouth.

Figure 2A:
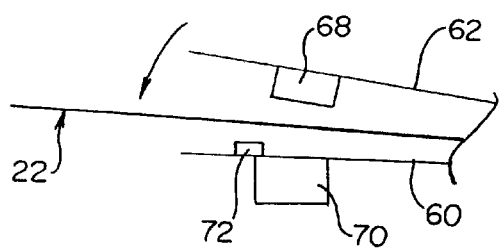
FIG. 2A is a detailed sectional view of the area denoted in FIG. 2 depicting the closure mechanism for a container housing a supply of surgical drapes.

Particularly now referring to FIG. 2A, the portion of the flanges 60 & 62 forming the mouth 64 are equipped with cooperating means to secure the cover 54 to the base 52, namely paired knobs 68 and knob receiving holes 70. Furthermore, at least one of the flanges 60/62 forming the container mouth 64 is equipped with a tensioning mechanism, here an upwardly projecting ridge 72 from the base flange 60 for engaging the drape 21 positioned for dispensing against the portion of the cover flange 62 forming the mouth 64, to prevent the outer most drape 22 of the continuous rolled length 20 from "creeping" or falling back into the dispenser 50.

The surgical drape 21 is preferably a blown polyethylene film, however plastic films or non-woven material compositions are suitably configured. Film thicknesses ranging from about 0.001 to 0.006 inches may be worked, with a 0.002 inch polyethylene film being preferred. Lines of weakness are preferably formed using a perforating wheel, blade or equivalent device having approximately 20–30 teeth per inch.

Each drape 21 of the continuous rolled length of surgical drapes 20 can be dimensioned to be 18 inches by 24 inches, with the stored and dispensed width for the continuous rolled length being roughly 7 inches. It will be understood, however, that other dimensions are contemplated and that those identified above are not exclusive. Supplies of 50 individual drapes as hereinabove dimensioned yield a very compact and highly manageable roll having a diameter less than about 4 inches (i.e., advantageously dimensioned for single hand holding).

The adhesive strip 32 is preferably a tacky variety and is applied adjacent to the major longitudinal edge 26 of the continuous rolled length of surgical drapes 20 to a thickness of about 0.008 inches, with the thickness being more a function of the performance associated with any given adhesive. However, in all events, the relationship between the thicknesses of the drape material and the thickness of the adhesive strip 32 in combination with the release liner 34 should be such that the thickness of the overlying adjacent longitudinal drape panels 42 having a collapsed zig-zag configuration 46 be substantially equivalent to the thickness of the adhesive strip 32 in combination with the release liner 34. In this way, a substantially "lump" free rolled supply of compact surgical drapes is provided.

The container 50 is generally a one piece thermoform, preferably a polyethylene, with its critical features being light weight and durable construction. Preferably the container is dimensioned to be held in one hand, thereby permitting one handed drape removal. A container about 8 inches long, 5 inches wide and 4 inches tall is capable of housing the preferred drape supply for dispensing therefrom as outlined hereinabove.

It will be understood that this disclosure, in many respects, is only illustrative. Changes may be made in details, particularly in matters of shape, size, material, and arrangement of parts without exceeding the scope of the invention. Accordingly, the scope of the invention is as defined in the language of the appended claims.

What is claimed is:

1. A configuration of surgical drapes for convenient dispensing and handling from a container, said configuration comprising a continuous rolled length of surgical drapes, each having opposing major and minor longitudinal edges and being separable from adjacent drapes by longitudinally spaced apart lines of weakness defined at regular intervals throughout said continuous length of surgical drapes, said length of surgical drapes having a folded accordion pleat along at least one of said major longitudinal edges thereof.

2. The configuration of surgical drapes of claim 1 wherein said continuous rolled length of surgical drapes further includes an adhesive strip contiguous to said major longitudinal edge of said continuous rolled length of surgical drapes, said adhesive strip carrying a removable release liner thereover.

3. The configuration of surgical drapes of claim 1 wherein said fold forms overlying adjacent longitudinal drape panels having a collapsed zig-zag cross section, each of said panels being delimited by spaced apart longitudinal creases.

4. The configuration of surgical drapes of claim 3 wherein said removable release liner partially overhangs said adhesive strip.

5. The configuration of surgical drapes of claim 4 wherein said minor longitudinal edge is positioned to be retained under the overhang of said removable release liner for especially easy handling and deployment of a dispensed drape.

6. The configuration of surgical drapes of claim 1 in combination with a container, said configuration of surgical drapes being removably housed within said container for easy dispensing of at least one drape from said configuration of surgical drapes.

7. The combination of claim 6 wherein said container includes a base and a cover, said cover being joined to said base at a common hinge for closure of said cover about said configuration of surgical drapes placed on said base.

8. The combination of claim 7 wherein said container further includes a drape dispensing mouth formed opposite said common hinge, said mouth configured to hold the outer most drape of said configuration of drapes in a position for easy grabbing and removal from said continuous rolled length of surgical drapes.

9. A package of surgical drapes for convenient dispensing and handling therefrom, comprising:
   a. a container having a base and a cover, said cover being joined to said base at a common hinge; and
   b. a continuous rolled length of surgical drapes removably housed within said container, said continuous roll having opposing major and minor longitudinal edges, each drape of said continuous roll being separable from adjacent drapes by longitudinally spaced apart lines of weakness defined at regular intervals throughout said continuous length of surgical drapes for easy dispensing of at least one drape from said continuous rolled length of surgical drapes, said length of surgical drapes having a folded accordion pleat along at least one of said major longitudinal edges thereof.

10. The configuration of surgical drapes of claim 9 wherein said continuous rolled length of surgical drapes further includes an adhesive strip adjacent said major longitudinal edge of said continuous rolled length of surgical drapes, said adhesive strip being equipped with a removable release liner thereover.

11. A method of storing and dispensing surgical drapes from a container comprising the steps of:
   a. supplying a continuous length of surgical drapes having a uniform width, each of said drapes being separable by longitudinally spaced apart lines of weakness defined at regular intervals;
   folding said continuous length of surgical drapes in a manner to reduce said uniform width;
   b. rolling the reduced width continuous length of surgical drapes;
   providing a container having a base and a cover, said cover being joined to said base at a common hinge for closure of said cover; and
   housing the rolled reduced width continuous length of surgical drapes within said container for dispensing at least one drape from said configuration of surgical drapes.

12. In a method of manufacturing a continuous rolled length of surgical drapes for convenient dispensing and handling, the steps of:
   a. accordion folding the longitudinal edges of a supply of drape material towards the centerline of said supply; and
   b. cutting said supply along said centerline to thereby form two lengths of fan folded surgical drape material.

13. In the method of claim 12, the further step of applying an adhesive about said centerline and a removable release liner thereupon, prior to cutting said supply along said centerline.

* * * * *